United States Patent [19]
Bober

[11] 4,001,667
[45] Jan. 4, 1977

[54] CONSTANT CURRENT-PULSE LED DRIVE CIRCUIT

[75] Inventor: Robert E. Bober, Framingham, Mass.

[73] Assignee: American Optical Corporation, Southbridge, Mass.

[22] Filed: May 2, 1975

[21] Appl. No.: 574,184

Related U.S. Application Data

[62] Division of Ser. No. 462,696, April 22, 1974, Pat. No. 3,902,806.

[52] U.S. Cl. .................... 323/1; 307/24; 307/33; 307/264; 323/21; 356/41
[51] Int. Cl.² ............................................ G05F 1/20
[58] Field of Search .............. 323/1, 4, 9, 19, 21, 323/22 T, 40; 307/24, 31–33, 44, 45, 56, 72, 75, 264, 265, 270; 356/41

[56] References Cited
UNITED STATES PATENTS

| | | | |
|---|---|---|---|
| 3,471,770 | 10/1969 | Haire | 323/1 |
| 3,647,299 | 3/1972 | Lavallee | 356/41 |
| 3,675,114 | 7/1972 | Nercessian | 307/32 X |
| 3,784,844 | 1/1974 | McGrogan, Jr. | 307/270 |

OTHER PUBLICATIONS

IBM Tech. Disc. Bull. vol. 11 No. 2, July 1968; p. 110.

*Primary Examiner*—Gerald Goldberg
*Attorney, Agent, or Firm*—Stephen A. Schneeberger; William C. Nealon; Howard R. Berkenstock, Jr.

[57] ABSTRACT

A circuit for use with an oximeter system which provides constant current pulses to light-emitting diodes in a sequential and cyclical manner. The circuit maintains magnitudes of pulses in the pulse train equal to certain other pulses in the pulse train over extremes of temperature variation, voltage variation, and time duration. Each diode is energized by a series of pulses having the same magnitude, although pulse magnitudes will vary from diode to diode. Therefore, light output from one light-emitting diode remains proportional to light output from the others.

2 Claims, 4 Drawing Figures

CONSTANT CURRENT-PULSE LED DRIVE CIRCUIT

This is a division of application Ser. No. 462,696 filed Apr. 22, 1974, now U.S. Pat. No. 3,902,806.

BACKGROUND OF THE INVENTION

1. Field of the Invention

The present invention generally relates to medical electronics devices, and more specifically relates to a lightemitting diode drive for use with an oximeter system.

2. Description of Prior Art

Oximeters have long been used to measure blood oxygen saturation. The greater the oxygen saturation, the redder are the red blood cells. If red light at a wavelength of 660 millimicrons (mu) is directed toward the blood sample, the amount of light reflected depends on how red the blood is, i.e., its oxygen content. The amount of reflected light increases with the oxygen saturation.

However, it has been recognized that an absolute measurement of the reflected red light is not a true indication of oxygen saturation. This is due to the fact that the oxygen content of the blood sample under test is affected not only by oxygen saturation, but also by the concentration of the hemoglobin in the blood. For example, even if the red blood cells are 100 percent saturated with oxygen, the amount of red light reflected may be very small if the concentration of red blood cells in the blood is low. For this reason, for many years the measurement of oxygen concentration has been performed by directing light at two wavelengths toward the blood sample. In addition to the 660-mu light, light at a wavelength of 805 millimicrons is also directed toward the sample (either simultaneously or sequentially with the 660-mu light). The amount of light at the higher wavelength reflected from the sample is dependent upon the concentration of the red blood cells in the sample, but is not affected by the oxygen saturation of these cells. Consequently, the 805-mu reflected light can be used as a reference to prevent the hemoglobin concentration from affecting the oxygen saturation measurement. Instead of reading only the amount of 660-mu light reflected from the sample, the ratio of the 805-mu reflected light to the 660-mu reflected light is measured. The red blood cell concentration affects both the numerator and the denominator of the ratio in the same way and thus does not affect the ratio itself. Thus the measurement is in effect made independent of the concentration of the red blood cells in the blood. Since only the denominator of the ratio is affected by the oxygen concentration, the ratio is an indication of the oxygen concentration.

Recently, light-emitting diodes (LEDs) have been employed as light sources for oximeters. In any oximeter utilizing two or more LEDs as two different light sources, (for example, as described above), it is important to maintain constant or proportional the intensities of the light emitted from the diodes. If the intensities of the two light emissions vary proportionally, there would be no appreciable error in the resulting measurement based on ratios of these two light measurements, since the ratio would not be affected.

Prior art circuitry for driving or energizing light sources to be used in this manner were burdened with problems caused by variations of ambient temperature, supply voltage, etc. Tungsten filament lamps combined with light-chopper wheels were employed; different wavelength light was obtained by passing the light through different filters (colored glass). This arrangement was extremely dependent upon voltage and operating life. The wavelength and intensity both shifted with use. Operating life was limited, since circuit parameters varied over long periods of time. Furthermore, in prior art drive circuitry usually multi-current sources were used, one for each diode. Thus, variations between individual sources created additional error. Accordingly, measurements made using prior art equipment had certain limitations and inaccuracies. The present invention provides a solution to these severe prior art problems.

SUMMARY OF THE INVENTION

The present invention relates to circuitry for supplying current to light-emitting diodes (LEDs) for use with an oximeter system. There is provided a current pulse generator for supplying a current pulse train or series of pulses, a control for maintaining constant the magnitude of each of the pulses and for making each pulse equal in magnitude or amplitude to only certain other predetermined pulses in the pulse train. The present invention provides additional sequential control for applying all pulses having the same magnitude to a preselected diode. In a further feature of the circuit, the number of diodes is selected to be equal to the number of different magnitudes of pulses generated. In a preferred embodiment of the present invention, the foregoing is provided in conjunction with a regulated power supply and an unregulated power supply, where the LEDs are mounted in a manner to ensure increased accuracy, stability, and patient safety.

It is advantageous for patient and physician alike to employ the present invention since it provides more stable, accurate, and reliable results than with prior art devices of this type.

It is thus an object of this invention to provide an improved oximeter system.

It is a further object of the present invention to provide an improved light source energizing circuit, which is capable of use with at least an oximeter system.

Further advantages and objects of the present invention will become apparent to one of reasonable skill in the art after referral to a detailed description of the appended drawings wherein:

DESCRIPTION OF THE PREFERRED EMBODIMENTS

Figure 1:
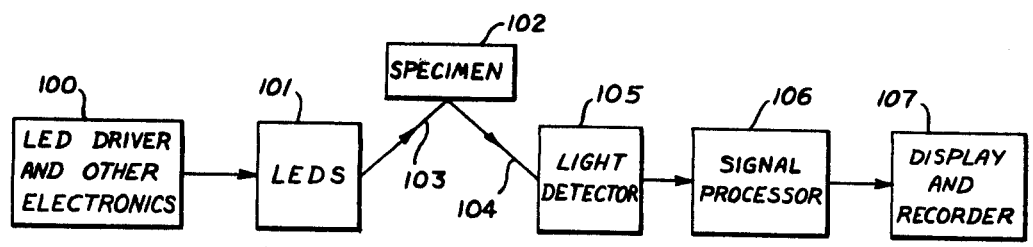
FIG. 1 depicts a functional block diagram of an oximeter system.

Referring to FIG. 1, an oximeter system is functionally depicted. LED driver and other electronics 100 energizes LEDs 101. Light intensity 103 is directed onto specimen 102 which reflects light 104 into light detector 105. Light detector 105 may typically be a photo-transistor which provides an electrical signal into signal processor 106. Signal processor 106 comprising standard electronic circuitry converts the electrical signal into useful information about specimen 102. This information is displayed and recorded as indicated by numeral 107. A more detailed description of an oximeter of this general type is provided in U.S. Pat. No. 3,647,299, issued Mar. 7, 1972, and assigned to the assignee of the present invention. Subject matter disclosed in this patent is incorporated herein by reference. The improvement of the present invention as it applies to oximeters replaces diode drivers 20, 22, and 24 in FIG. 1 of that patent.

Figure 2:
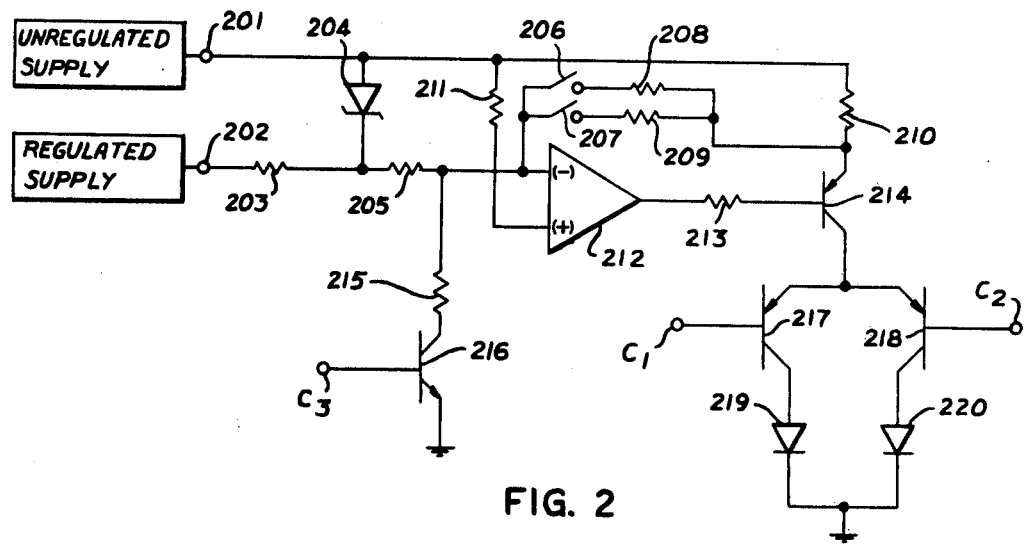
FIG. 2 depicts a schematic diagram of an illustrative embodiment of the present invention.

Referring to FIG. 2, an unregulated power supply is connected to terminal 201 and a regulated power supply is connected to terminal 202. A large amount of current is needed to drive light-emitting diodes 210 and 220. This current may be about one ampere or more. Accordingly, an unregulated supply is generally more desirable than a regulated supply for this magnitude of current in oximetry applications because of size and economic factors. However, because of the requirements of constant current magnitude or constant current proportion, the present invention is needed to compensate for at least the fluctuations of voltage in the unregulated supply.

Terminal 201 is conductively connected to the anode of zener diodes 204, one end of resistor 211, and one end of resistor 210. Terminal 202 is conductively connected to one end of resistor 203, the other end being connected to the cathode of zener diode 204 and to one end of resistor 205. The other end of resistor 205 is connected to the inverting input of operational amplifier 212, one end of resistor 215, and switches 206 and 207. The other end of resistor 215 is connected to the collector of transistor 216 the emitter of which is connected to ground and the base of which is connected to terminal C3. The other end of resistor 211 is connected to the non-inverting input of operational amplifier 212, the output of which is conducted to one end of resistor 213. The other end of resistor 213 is connected to the base of transistor 214. The emitter of transistor 214 is connected to the other end of resistor 210, and to one end of resistor 208 and one end of resistor 209. The other ends of resistors 208 and 209 are connected to switches 206 and 207 respectively. The collector of transistor 214 is connected to emitters of transistors 217 and 218. The bases of transistors 217 and 218 are connected to terminals C1 and C2 respectively and the collectors are connected to the anodes of light-emitting diodes 219 and 220 respectively. The cathodes of both diodes are connected to ground and to a heat sink (not shown).

Figures 3, 4:
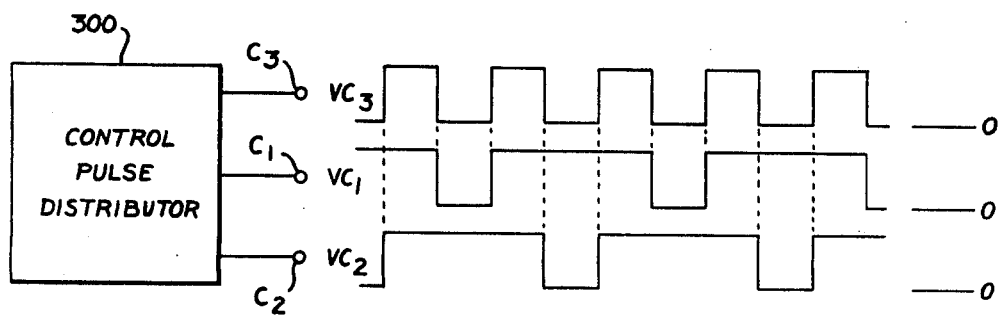
FIG. 3 depicts a block diagram of circuitry to be used in conjunction with FIG. 2.
FIG. 4 depicts control pulse waveforms generated by the circuitry of FIG. 3.

The foregoing description of circuit inter-connection should be considered in conjunction with FIG. 3. Control pulse distributor 300 has output terminals $C_1$, $C_2$, and $C_3$ which are the same terminals so designated in FIG. 2. Control pulse distributor 300 is comprised of known circuitry such as a digital counter and diode gates which provides the distribution of control pulses in a predetermined sequence. In FIG. 4, the type of pulses provided by distributor 300 is depicted. $VC_3$ represents the pulse train which is applied to terminal $C_3$, $VC_2$ represents the pulse train which is applied to terminal $C_2$, and $VC_1$ represents the pulse train which is applied to terminal $C_1$ of FIG. 2. Pulse $VC_3$ is provided only when there is positive voltage applied at both terminals $C_1$ and $C_2$, reverse biasing the base emitter junctions of transistors 217 and 218 and thereby preventing conduction therethrough.

The "zero" base lines of FIG. 4 (marked "0") represent ground level. Therefore $VC_3$ is a positive going pulse, and $VC_1$ and $VC_2$ are negative going pulses, going from some positive voltage to ground. This pulse distribution will be further described below in connection with the operation of the circuitry of FIG. 2.

In operation, current passing through diodes 219 and 220 causes light to be emitted at wavelengths characteristic of those diodes. The emitted light is directed on the blood sample or specimen to be examined. Two diodes are employed in the preferred embodiment, but more than two diodes can be utilized. More diodes would require an equally increased number of switching components and output pulse trains from pulse distributor 300.

Negative going pulses from pulse distributor 300 and shown in FIG. 4 are applied to terminal $C_1$ causing transistor 217 to conduct. Simultaneously, positive voltage is applied to the base of transistor 218 on terminal $C_2$ causing transistor 218 not to conduct, and vice-versa. Therefore, light-emitting diodes 219 and 220 emit light mutually exclusively and in the arrangement shown. Both transistors 217 and 218 are commanded off during the time period associated with $VC_3$. Each diode energization burden placed upon the unregulated supply is separated from the next energization burden by the duration of $VC_3$. This separation provides settling time for the amplifiers and the power supplies. In this manner, the LEDs are sequentially and cyclically energized. During the duration of $VC_3$, transistor 216 is biased on and the inverting input of operational amplifier 212 is substantially reduced. Therefore, output of operational amplifier 212 is made substantially more positive and transistor 214 is cut off (cooperating with the positive voltages applied to the bases of transistors 217 and 218 to ensure no current flow through either of the light-emitting diodes).

In the preferred embodiment, both LEDs 219 and 220 are attached to the same heat sink at ground potential. This ensures that the junctions of both diodes remain close together in temperature. Most high power light-emitting diodes are constructed with their cathodes electrically connected to mounting studs. With the circuit of the present invention, light-emitting diodes have their cathodes connected at the same potential. This common connection permits more intimate thermal contact with the desired environment and results in better heat balance between the various diodes. Also, in certain applications of the oximeter where the light-emitting diodes are located at the bedside of hospitalized patients the heat sink connection to ground potential provides additional safety. The time of pulse VC3 permits diodes 219 and 220 to conduct heat developed to the heat sink mentioned. The judicious placement of these diodes and their connection to the same heat sink to expose both to the same temperature is an additional feature of the present invention.

The regulated supply provides regulated voltage to resistor 203 and a comparatively small amount of current is drained from this supply. When the unregulated supply, for example drops in voltage, the voltage drop across zener diode 204 remains constant and the voltage at the junction of the cathode of zener diode 204 drops likewise. This decreasing voltage is sensed at the inverting input of operational amplifier 212. However, the non-inverting or positive input of operational amplifier 212 is not connected to ground, but is referenced to the unregulated supply. Therefore, the two inputs to operational amplifier 212 vary in the same direction and by the same amount. Accordingly, output of operational amplifier 212 remains constant measured with respect to the unregulated supply voltage as the unregulated supply voltage varies. Therefore, the voltage developed across resistor 210, the emitter-base junction of transistor 214, and resistor 213 remain constant. Thus, a constant current is provided on the collector of transistor 214 although the unregulated supply voltage varies. Transistors 214 is connected to provide a high impedance output from its collector. Current going to either light-emitting diode is thus independent of light-emitting diode voltage drop, or line or conductor impedance.

Switches 206 and 207 are shown in an open state condition. They are shown as mechanical switches for purposes of clarity of illustration, but in the preferred embodiment they are semi-conductor switches (transistors) also operated by VC1 and VC2. When transistor 217 conducts, only switch 207 closes, but when transistor 218 conducts, 206 is closed and 207 is open. Resistors 208 and 209 are therefore alternatively connected into and out of the circuit and form a feedback bridge to the input of amplifier 212.

The values of resistance of resistors 208 and 209 are different. Thus, closure of these switches changes the resistance value connected between the inverting input of operational amplifier 212 and the emitter of transistor 214. The connection of either of these resistances into the circuit changes the gain of amplifier 212 in a manner well known in the art. But, this arrangement also provides a current flow path through resistors 208 or 209 in a direction dictated by relative magnitudes of voltages at either side of the then-connected resistor. The net effect is to control the magnitude of current passed by transistor 214.

Accordingly, the current pulse developed by the conduction of transistors 217 or 218 has constant magnitude for the duration of the pulse but the pulse conducted to one diode is different in magnitude from the magnitude of the current pulse conducted to the other diode. This difference in voltage or current magnitude is necessary since the diode drive requirements are usually different. Each magnitude is selected to be optimum for a particular diode.

The current pulses to diodes 219 and 220 are each proportional to the same circuit parameters, i.e.: the value of resistor 210, the voltage of zener diode 204, and either the value of resistance 208 divided by the value of resistor 205 or the value of resistor 209 divided by the value of resistor 205. These resistors are selected to have the same temperature coefficients so that any change in one resistance due to temperature variation is tracked or compensated for by the other resistor.

Employing this circuitry in an oximeter, as noted, the ratio of the two light outputs is at least as important as absolute light output in order to maintain accuracy. Because of judicious selection of resistors having the same temperature coefficients, because of the judicious mounting of light-emitting diodes at a particular advantageous position in the instrument, and because of the above-described circuitry of the present invention, the two light-emitting diode currents are kept proportional to each other. The current drive ratio is thus made independent of certain variable parameters such as: gain of operational amplifier 212, gain of transistors 214, 217, and 218, voltage drops of light-emitting diodes 219 and 220, connecting wire impedances associated with these components, and voltage of the unregulated supply.

The invention may be embodied in yet other specific forms without departing from the spirit or essential characteristics thereof. Thus, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A circuit for supplying current drive to a plurality of light-emitting diodes, which may each require different drive-current, said circuit being capable of use with an oximeter system, said circuit comprising at least one electrical power supply, means for generating a series of current pulses from said supply, means for controlling the magnitude of each of said pulses of said series to be constant and equal to only certain other pulses of said series, according to the respective drive-current requirements of the light emitting diodes, and means for sequentially and cyclically applying said constant magnitude pulses to said plurality of diodes so that each of said diodes is energized only by pulses having the same magnitude.

2. A circuit as recited in claim 1 wherein said at least one electrical power supply comprises a regulated power supply and an unregulated power supply, and said circuit further comprises current regulator transistor means energized by said unregulated supply, operational amplifier means for biasing said transistor means from said unregulated supply, feedback bridge means connected between the input of said operational amplifier means and said current regulator transistor means for establishing said magnitude of said each of said pulses, and control pulse distribution means for simultaneously controlling said feedback bridge means and said applying means.

* * * * *